United States Patent
Weinschenk, III et al.

(10) Patent No.: US 7,781,571 B2
(45) Date of Patent: Aug. 24, 2010

(54) OPHTHALMIC LENS MATERIALS CONTAINING CHROMOPHORES THAT ABSORB BOTH UV AND SHORT WAVELENGTH VISIBLE LIGHT

(75) Inventors: Joseph I. Weinschenk, III, Fort Worth, TX (US); Douglas C. Schlueter, Azle, TX (US); David L. Jinkerson, Benbrook, TX (US)

(73) Assignee: Alcon, Inc., Hunenberg (CH)

( * ) Notice: Subject to any disclaimer, the term of this patent is extended or adjusted under 35 U.S.C. 154(b) by 51 days.

(21) Appl. No.: 12/187,642

(22) Filed: Aug. 7, 2008

(65) Prior Publication Data

US 2009/0043105 A1 Feb. 12, 2009

Related U.S. Application Data

(60) Provisional application No. 60/954,988, filed on Aug. 9, 2007.

(51) Int. Cl.
*C09B 29/12* (2006.01)
(52) U.S. Cl. .................. 534/799; 351/159; 351/160 R; 534/590
(58) Field of Classification Search .................. 534/799
See application file for complete search history.

(56) References Cited

U.S. PATENT DOCUMENTS

| | | |
|---|---|---|
| 4,390,676 A | 6/1983 | Loshaek |
| 4,528,311 A | 7/1985 | Beard et al. |
| 4,611,061 A | 9/1986 | Beard et al. |
| 4,652,656 A | 3/1987 | Besecke et al. |
| 4,716,234 A | 12/1987 | Dunks et al. |
| 4,795,461 A | 1/1989 | Lindqvist et al. |
| 4,803,254 A | 2/1989 | Dunks et al. |
| 5,147,902 A | 9/1992 | Ichikawa et al. |
| 5,290,892 A | 3/1994 | Namdaran et al. |
| 5,331,073 A | 7/1994 | Weinschenk, III et al. |
| 5,470,932 A | 11/1995 | Jinkerson |
| 5,543,504 A | 8/1996 | Jinkerson |
| 5,637,726 A | 6/1997 | Collins et al. |
| 5,693,095 A | 12/1997 | Freeman et al. |
| 6,166,218 A | 12/2000 | Ravichandran et al. |
| 6,242,551 B1 | 6/2001 | Tsuzuki et al. |
| 6,310,215 B1 | 10/2001 | Iwamoto |
| 6,320,008 B2 | 11/2001 | Tsuzuki et al. |
| 6,806,337 B2 | 10/2004 | Schlueter et al. |
| 6,846,897 B2 | 1/2005 | Salamone et al. |
| 6,852,793 B2 | 2/2005 | Salamone et al. |
| 6,872,793 B1 | 3/2005 | Schlueter |
| 6,878,792 B2 | 4/2005 | Ichinohe |
| 7,037,954 B2 | 5/2006 | Baba et al. |
| 7,067,602 B2 | 6/2006 | Benz et al. |
| 7,098,283 B2 | 8/2006 | Lai |
| 7,101,949 B2 | 9/2006 | Salamone et al. |
| 7,232,896 B2 | 6/2007 | Miki et al. |
| 7,278,737 B2 | 10/2007 | Mainster et al. |
| 7,326,423 B2 | 2/2008 | Pearson et al. |
| 7,375,234 B2 | 5/2008 | Sharpless et al. |
| 7,381,762 B2 | 6/2008 | Xia |
| 7,585,900 B2 * | 9/2009 | Cordova et al. ............. 523/107 |
| 2002/0042653 A1 | 4/2002 | Copeland et al. |
| 2006/0197067 A1 | 9/2006 | Xia et al. |
| 2006/0241263 A1 | 10/2006 | Lai |
| 2006/0252850 A1 | 11/2006 | Jani et al. |
| 2007/0092830 A1 | 4/2007 | Lai et al. |
| 2007/0092831 A1 | 4/2007 | Lai et al. |
| 2008/0090937 A1 | 4/2008 | Jinkerson et al. |
| 2008/0242818 A1 | 10/2008 | Benz et al. |
| 2008/0266519 A1 | 10/2008 | Schlueter |
| 2009/0043007 A1 * | 2/2009 | Weinschenk et al. ........ 523/106 |

FOREIGN PATENT DOCUMENTS

| | | |
|---|---|---|
| CN | 1727338 | 2/2006 |
| EP | 1 431 350 B1 | 2/2008 |
| EP | 1 033 590 B1 | 5/2008 |
| JP | 1 299560 | 4/1989 |
| JP | 2005053058 | 3/2005 |
| JP | 2009013148 | 1/2009 |
| WO | WO9512279 A1 | 4/1995 |
| WO | 00/04848 A1 | 2/2000 |
| WO | 2006/057824 A3 | 6/2006 |
| WO | 2006/119304 A1 | 11/2006 |
| WO | 2007/050394 A2 | 5/2007 |
| WO | 2007050395 A2 | 5/2007 |
| WO | 2008109624 A2 | 9/2008 |

OTHER PUBLICATIONS

Jin, et al., Synthesis and photoinduced birefringence of polymethacrylates with azo-substituted pyrazoline in the side chain, Materials Chemistry and Physics 2003, pp. 246-252, 82.

Macchia, et al., "Role of the benzylic hydroxyl group of adrenergic catecholamines in eliciting a-adrenergic activity. Synthesis and al- and a2-adrenergic activity of 3-phenyl-3-piperidinols and their desoxy analogs." Eur J Med Chem, 1995, 869-880, vol. 30, Elsevier, Paris.

Kratts, et al., "Sharp cutoff filters in intraocular lenses optimize the balance between light reception and light protection." J Cataract Refract Surg, May 2007, 879-887, vol. 33, Elsevier, Inc.

Kolb, et al., "Click Chemistry: Diverse Chemical Function from a Few Good Reactions." Angew. Chem. Int. Ed, 2001, 2004-2021, vol. 40, Wiley-VCH, Verlag GmbH, Weinheimm Germany.

Rostovtsev, et al., "A Stepwise Huisgen Cycloaddition Process: Copper (I)-Catalyzed Regioselective 'Ligation' of Azides and Terminal Alkynes." Angew. Chem. Int. Ed. 2002, 2596-2599, vol. 41, No. 14, Wiley-VCH, Verlag GmbH, Weinheim, Germany.

(Continued)

*Primary Examiner*—Fiona T Powers
(74) *Attorney, Agent, or Firm*—Patrick M. Ryan

(57) ABSTRACT

Chromophores that absorb both UV and short wavelength visible light are disclosed. The chromophores are particularly suitable for use in intraocular lens materials.

12 Claims, No Drawings

OTHER PUBLICATIONS

Sparrow, et al., "Blue Light-Absorbing Intraocular Lens and Retinal Pigment Epithelium Protection in vitro." J Cataract Refract Surg, Apr. 2004, 873-878, vol. 30, Elsevier, Inc.

Sparrow, et al., "The Lipofuscin Fluorophore A2E Mediates Blue Light-Induced Damage to Retinal Pigmented Epithelial Cells," Invest Ophthalmol Vis Sci, Jun. 2000, 1981-1989, vol. 41, No. 7.

Sparrow, et al., "Blue Light-Induced Apoptosis of A2E-Containing RPE: Involvement of Caspase-3 and Protection by Bcl-2," Invest Ophthalmol Vis Sci , May 2001, 1356-1362, vol. 42, No. 6.

Zhu, et al., "Synthesis of aryl azides and vinyl azides via proline-promoted CuI-catalyzed coupling reactions," Chem. Commun., 2004, 888-889.

* cited by examiner

OPHTHALMIC LENS MATERIALS CONTAINING CHROMOPHORES THAT ABSORB BOTH UV AND SHORT WAVELENGTH VISIBLE LIGHT

This application claims priority to U.S. Provisional Application, U.S. Ser. No. 60/954,988 filed Aug. 9, 2007.

FIELD OF THE INVENTION

This invention is directed to chromophores. In particular, this invention relates to chromophores that absorb both UV and short wavelength light.

BACKGROUND OF THE INVENTION

Many UV light absorbers are known as ingredients for polymeric materials used to make ophthalmic lenses. UV absorbers are preferably covalently bound to the polymeric network of the lens material instead of simply physically entrapped in the material to prevent the absorber from migrating, phase separating or leaching out of the lens material. Such stability is particularly important for implantable ophthalmic lenses, especially intraocular lenses (IOLs), where the leaching of the UV absorber may present both toxicological issues and lead to the loss of UV blocking activity in the implant.

Numerous copolymerizable benzatriazole, benzophenone and triazine UV absorbers are known. Many of these UV absorbers contain conventional olefinic polymerizable groups, such as methacrylate, acrylate, methacrylamide, acrylamide or styrene groups. Copolymerization with other ingredients in the lens materials, typically with a radical initiator, incorporates the UV absorbers into the resulting polymer chain. Incorporation of additional functional groups, on a UV absorber may influence one or more of the UV absorber's UV absorbing properties, solubility or reactivity. If the UV absorber does not have sufficient solubility in the remainder of the ophthalmic lens material ingredients or polymeric lens material, the UV absorber may coalesce into domains that could interact with light and result in decreased optical clarity of the lens.

Examples of polymeric ophthalmic lens materials that incorporate UV absorbers can be found in U.S. Pat. Nos. 5,290,892; 5,331,073 and 5,693,095.

Likewise, copolymerizable short wavelength light absorbing chromophores are known as ingredients for polymeric materials used to make ophthalmic lenses. Blue-light absorbing chromophores include those disclosed in U.S. Pat. Nos. 5,470,932 and 5,543,504.

In order to obtain polymeric lens materials that absorb both UV and short wavelength visible light (e.g., 400-500 nm), it is common to add separate UV-absorbing and short wavelength light-absorbing chromophores to the polymeric materials. For example, the AcrySof® Natural IOL product, which is commercially available from Alcon Laboratories, Inc., contains a UV absorber and a blue-light absorber.

Having a single chromophore that absorbs both UV and short wavelength visible light would be advantageous. Such a single chromophore would reduce the number of components that are added to a lens material formulation and reduce disruption to the primary polymer chain structure produced by the lens formulation's primary monomer constituents.

SUMMARY OF THE INVENTION

The present invention provides chromophores that absorb both UV and short wavelength visible light. These chromophores are suitable for use in ophthalmic lenses, including contact lenses. They are particularly useful in implantable lenses, such as IOLs.

DETAILED DESCRIPTION OF THE INVENTION

Unless indicated otherwise, all ingredient amounts expressed in percentage terms are presented as % w/w.

The chromophores of the present invention are represented by the formula

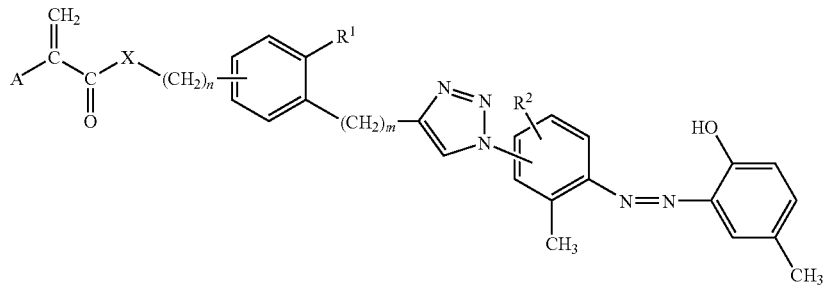

wherein
A=H or $CH_3$;
X=O or NH;
n=2-6;
m=0-6;
$R^1$=H, OH, $C_1$-$C_4$ alkyl, or $C_1$-$C_4$ alkoxy; and
$R^2$=H or OH.

A preferred chromophore of the present invention has
A=$CH_3$;
X=O;
n=2;
m=0;
$R^1$=H; and
$R^2$=H.

The synthesis of the chromophores of the present invention is described below (Scheme 1). Aromatic alkyne (2) is synthesized in 2 steps from 4-bromo-phenethyl alcohol. Sonogishira coupling of the aryl bromide with trimethylsilylacetylene, followed by deprotection and esterification with methacryloyl chloride produces a methacrylate functionalized aryl alkyne (2). Alternatively, esterification with 4-vinylbenzoic acid using carbodiimide coupling will produce a vinyl-functional chromophore. The azo coupling product from 4-iodo-2-methylaniline with p-cresol is converted to the aryl azide (4) by proline promoted CuI-catalyzed coupling (Zhu, W.; Ma, D. *Chem. Commun.* 2004, 888). This is then combined with an equimolar amount of aryl akyne (2) and a catalytic amount of CuBr to yield 1,2,3-triazole (5).

6,806,337; 6,528,602; and 5,693,095. In the case of IOLs, any known IOL device material is suitable for use in the compositions of the present invention. Preferably, the ophthalmic device materials comprise an acrylic or methacrylic device-forming monomer. More preferably, the device-forming monomers comprise a monomer of formula [II]:

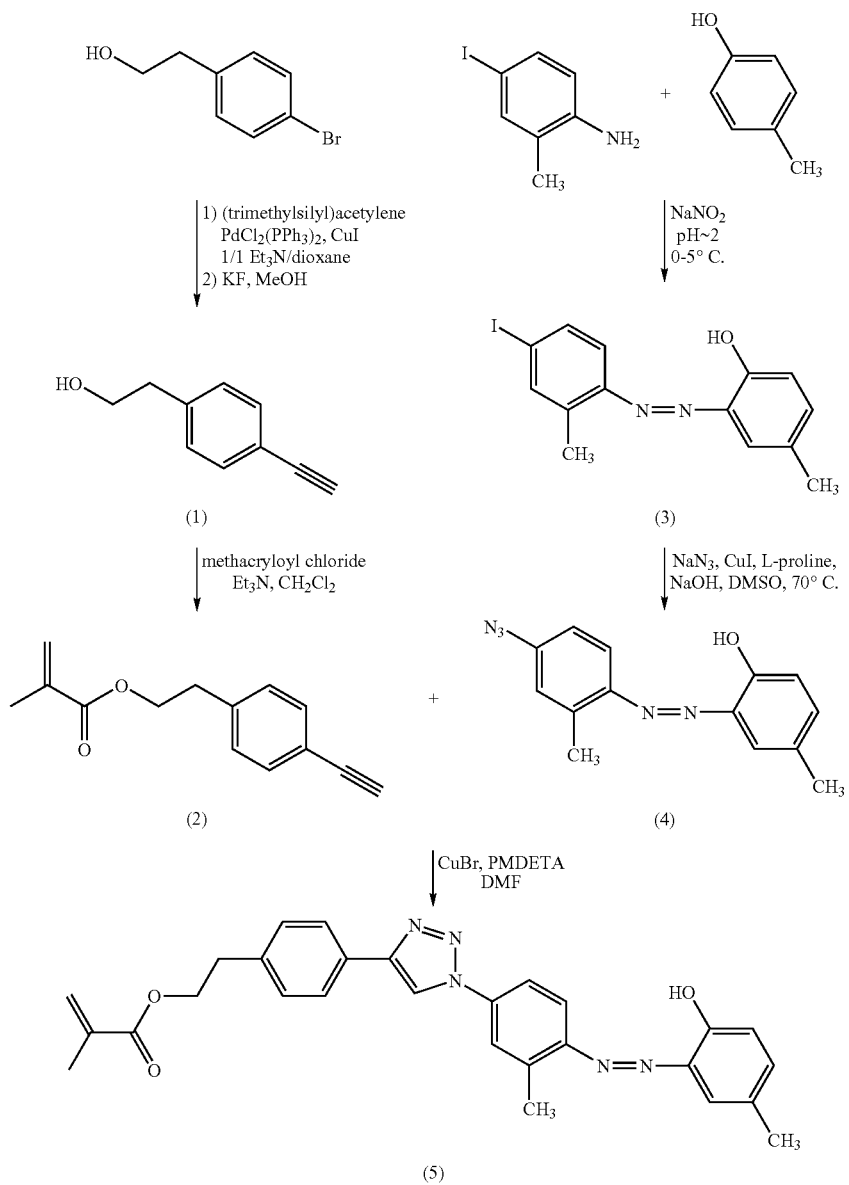

The chromophores of the present invention are particularly suitable for use in IOLs. IOL materials will generally contain from 0.1 to 5% (w/w) of a chromophore of the present invention. Preferably, IOL materials will contain from 0.5 to 3% (w/w) of a chromophore of the present invention. Such device materials are prepared by copolymerizing the chromophores of the present invention with other ingredients, such as device-forming materials and cross-linking agents.

Many device-forming monomers are known in the art and include both acrylic and silicone-containing monomers among others. See, for example, U.S. Pat. Nos. 7,101,949; 7,067,602; 7,037,954; 6,872,793 6,852,793; 6,846,897;

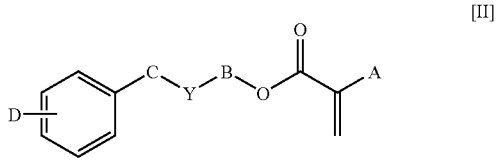

where in formula [II]:

A is H, $CH_3$, $CH_2CH_3$, or $CH_2OH$;

B is $(CH_2)_m$ or $[O(CH_2)_2]_z$;

C is $(CH_2)_w$;

m is 0-6;

z is 1-10;

Y is nothing, O, S, or NR', provided that if Y is O, S, or NR', then B is $(CH_2)_m$;

R' is H, $CH_3$, $C_{n'}H_{2n'+1}$ (n'=1-10), iso-$OC_3H_7$, $C_6H_5$, or $CH_2C_6H_5$;

w is 0-6, provided that m+w≦8; and

D is H, $C_1$-$C_4$ alkyl, $C_1$-$C_4$ alkoxy, $C_6H_5$, $CH_2C_6H_5$ or halogen.

Preferred monomers of formula [II] are those wherein A is H or $CH_3$, B is $(CH_2)_m$, m is 1-5, Y is nothing or O, w is 0-1, and D is H. Most preferred are benzyl methacrylate; 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

Monomers of formula [II] are known and can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding methacrylic acid to the conjugate alcohol and catalyzing with a carbodiimide or mixing the conjugate alcohol with methacryloyl chloride and a base such as pyridine or triethylamine.

Device materials generally comprise a total of at least about 75%, preferably at least about 80%, of device-forming monomers.

In addition to a chromophore of the present invention and a device-forming monomer, the device materials of the present invention generally comprise a cross-linking agent. The cross-linking agent used in the device materials of this invention may be any terminally ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2$=$C(CH_3)C$(=O)O—$(CH_2CH_2O)_p$—$C$(=O)$C(CH_3)$=$CH_2$ where p=1-50; and $CH_2$=$C(CH_3)C$(=O)$O(CH_2)_tO$—$C$(=O)$C(CH_3)$=$CH_2$ where t=3-20; and their corresponding acrylates. A preferred cross-linking monomer is $CH_2$=$C(CH_3)C$(=O)O—$(CH_2CH_2O)_p$—$C$(=O)$C(CH_3)$=$CH_2$ where p is such that the number-average molecular weight is about 400, about 600, or about 1000.

Generally, the total amount of the cross-linking component is at least 0.1% by weight and, depending on the identity and concentration of the remaining components and the desired physical properties, can range to about 20% by weight. The preferred concentration range for the cross-linking component is 0.1-17% (w/w).

Suitable polymerization initiators for device materials containing a chromophore of the present invention include thermal initiators and photoinitiators. Preferred thermal initiators include peroxy free-radical initiators, such as t-butyl (peroxy-2-ethyl)hexanoate and di-(tert-butylcyclohexyl)peroxydicarbonate (commercially available as Perkadox® 16 from Akzo Chemicals Inc., Chicago, Ill.). Initiators are typically present in an amount of about 5% (w/w) or less. The total amount of initiator is customarily not included when determining the amounts of other ingredients.

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

In addition to IOLs, the materials of the present invention are also suitable for use in other ophthalmic devices, such as contact lenses, keratoprostheses, and corneal inlays or rings.

The invention will be further illustrated by the following examples, which are intended to be illustrative, but not limiting.

EXAMPLE 1

Synthesis of (1)

A flask is flushed with $N_2$ and charged with 4-bromo-phenethyl alcohol (20 mmol) and dissolved in 1/1 $Et_3N$/dioxane. Bis(triphenylphosphine)palladium(II) dichloride ($PdCl_2(PPh_3)_2$) (0.2 mmol) is added, followed by 0.4 mmol of CuI. Trimethylsilylacetylene (24 mmol) is added drop-wise to the reaction mixture. The reaction mixture is stirred overnight under $N_2$. The solvent is removed under vacuum and the resulting liquid is extracted by washing with ethyl ether. The ethyl ether extracts are combined and washed with $H_2O$, then dried over anhydrous sodium sulfate. The solvent is removed under vacuum and the product is purified by column chromatography. The purified product is placed in a $N_2$-flushed flask and dissolved in methanol. Potassium fluoride (65 mmol) is added and the reaction stirred under a $N_2$ blanket for 16 h. The reaction mixture is poured into $CH_2Cl_2$ and extracted with $H_2O$, then dried over $Na_2SO_4$, filtered and the solvent is removed under vacuum. The resulting product is purified by column chromatography to yield 2-(4-ethynyl-phenyl)-ethanol (2).

EXAMPLE 2

Synthesis of (2)

A flask is flushed with $N_2$ and charged with 15 mmol of (2), 17 mmol of triethylamine and $CH_2Cl_2$. The solution is cooled in an ice water bath and methacryloyl chloride (17 mmol) is added drop-wise with stirring. Once the addition is complete, the cold bath is removed and the reaction stirred for 16 hr under a $N_2$ blanket. The reaction mixture is washed with 2 N HCl then washed with $H_2O$, and dried over anhydrous $Na_2SO_4$. The solvent is removed under vacuum and the resulting crude product is purified by column chromatography to yield methacrylate (2).

EXAMPLE 3

Synthesis of (3)

A flask is charged with 100 mmol of boric acid followed by 6N HCl solution to adjust the reaction solution to a pH of 2. Once the salt dissolves, 20 mmol of 4-iodo-2-methylaniline is added to the reaction solution, followed by enough ice to reduce solution temperature to 0° C. In a separate flask, 20 mmol of sodium nitrite ($NaNO_2$) is dissolved in ice water. The $NaNO_2$ solution is added drop-wise with constant stirring to the 4-iodo-2-methylaniline solution. The pH of the reaction solution is maintained by addition of 6N HCl. After the $NaNO_2$ solution addition is complete, ice is added to maintain the 0° C. reaction temperature. A $3^{rd}$ flask is charged with 20 mmol of p-cresol, water and 2.5 N NaOH (20 mmol), which is then added drop wise to the ice cooled reaction with constant stirring. The reaction mixture is allowed to stir for 15 min at pH 2.0-2.5. NaOH (2.5 N) is then added in small aliquots to the reaction solution to increase the pH to 8.5. The reaction solution is allowed to warm to room temperature. Dibasic sodium phosphate solution (100 mmol) is added and the pH is adjusted to 6.0 with 6 N HCl. The product is filtered, rinsed with ice water and air dried. The product is purified by column chromatography to yield 2-(4-iodo-2-methyl-phenylazo)-4-methyl-phenol (3).

EXAMPLE 4

Synthesis of (4)

A flask is flushed with $N_2$ and charged with 10 mmol of (3), 12 mmol of $NaN_3$, 1 mmol of CuI, 2 mmol of L-proline, 2 mmol of NaOH and DMSO. The reaction flask is immersed in an oil bath and heated to 70° C. under a $N_2$ blanket for 10 hr. The reaction mixture is then allowed to cool to room temperature and ethyl acetate is added and the solution is washed with water. The organic layer is separated, and the aqueous layer is extracted with ethyl acetate. The combined organic layers are washed with brine, dried over anhydrous $Na_2SO_4$, and the solvent is removed under vacuum. The resulting product was purified by column chromatography. to yield aryl azide (4).

EXAMPLE 5

Synthesis of (5)

A flask containing a PTFE coated stir bar is flushed with $N_2$ and charged with 15 mmol of aryl azide (4), 15 mmol of aryl acetylene (2), N,N-dimethylformamide, 3.0 mmol of N,N,N',N'',N''-pentamethyldiethylenetriamine, and 1.5 mmol of CuBr. The flask is stirred 20 h at ambient temperature. The reaction mixture is then exposed to air and purified by passing through a chromatographic alumina column. The eluent is collected and the solvent is removed under vacuum to yield product (5).

EXAMPLES 6-9

Copolymerization of a Chromophore with a Device-Forming Monomer

A vial is charged with ingredients as listed in Table 1 except for the initiator. The solution is mixed thoroughly and degassed by bubbling with $N_2$. The initiator is added and the solution is again mixed thoroughly. The solution is filtered through a 0.2 micron PTFE filter and transferred to polypropylene molds. The molds are heated in a mechanical convection oven at 70° C. for 1 hr, then 110° C. for 2 hrs. The resulting copolymer samples are removed from the polypropylene molds and extracted in refluxing acetone for at least 3 hr, then rinsed with fresh acetone and allowed to air dry. The extracted polymer is dried under vacuum at 70° C. for at least 3 hr.

TABLE 1

Representative Copolymer Formulations

| Ingredient | Amount (% w/w) | | | |
| --- | --- | --- | --- | --- |
| | 6 | 7 | 8 | 9 |
| PEA | 65.0 | 80.0 | 0.0 | 65.0 |
| PEMA | 29.95 | 0.0 | 0.0 | 31.25 |
| PBMA | 0.0 | 0.0 | 82.15 | 0.0 |
| HEMA | 0.0 | 14.95 | 0.0 | 0.0 |
| PEG(1000)DMA | 0.0 | 0.0 | 15.0 | 0.0 |
| EGDMA | 0.0 | 0.0 | 1.0 | 0.0 |
| BDDA | 3.2 | 3.2 | 0.0 | 3.2 |
| o-MTP | 1.8 | 1.8 | 1.8 | 0.0 |
| Chromophore (5) | 0.05 | 0.05 | 0.05 | 0.5 |
| Perkadox ® 16S | 1.0 | 1.0 | 1.0 | 1.0 |

PEA = 2-phenylethyl acrylate
PEMA = 2-phenylethyl methacrylate
PBMA = 4-phenylbutyl methacrylate
HEMA = 2-hydroxyethyl methacrylate
PEG(1000)DMA = polyethylene glycol (1000) dimethacrylate
EGDMA = ethylene glycol dimethacrylate
BDDA = 1,4-butanediol diacrylate
oMTP = o-methallyl Tinuvin P This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

We claim:
1. A chromophore of the formula

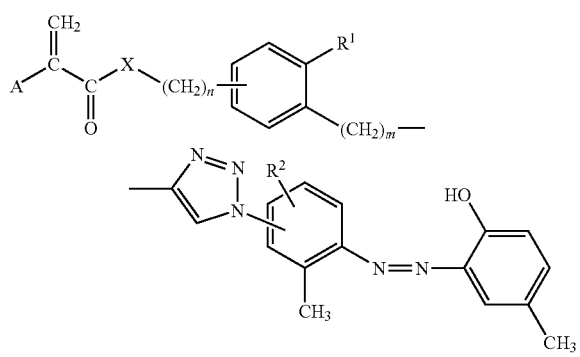

wherein
A=H or $CH_3$;
X=O or NH;
n=2-6;
m=0-6;
$R^1$=H, OH, $C_1$-$C_4$ alkyl, or $C_1$-$C_4$ alkoxy; and
$R^2$=H or OH.

2. The chromophore of claim 1 wherein
A=$CH_3$;
X=O;
n=2;
m=0;
$R^1$=H; and
$R^2$=H.

3. An ophthalmic device material comprising the chromophore of claim 1 and a device-forming monomer selected from the group consisting of acrylic monomers and silicone-containing monomers.

4. The ophthalmic device material of claim 3 wherein the ophthalmic device material comprises from 0.1 to 5% (w/w) of the chromophore.

5. The ophthalmic device material of claim 4 wherein the ophthalmic device material comprises from 0.5 to 3% (w/w) of the chromophore.

6. The ophthalmic device material of claim 3 wherein the ophthalmic device material comprises a device-forming monomer of formula [II]:

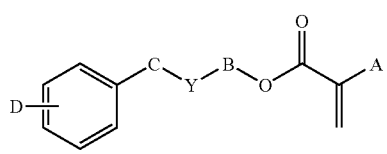

[II]

where in formula [II]:
A is H, $CH_3$, $CH_2CH_3$, or $CH_2OH$;
B is $(CH_2)_m$ or $[O(CH_2)_2]_z$;
C is $(CH_2)_w$;
m is 0-6;
z is 1-10;
Y is nothing, O, S, or NR', provided that if Y is O, S, or NR', then B is $(CH_2)_m$;
R' is H, $CH_3$, $C_{n'}H_{2n'+1}$ (n'=1-10), iso-$OC_3H_7$, $C_6H_5$, or $CH_2C_6H_5$;
w is 0-6, provided that m+w≦8; and
D is H, $C_1$-$C_4$ alkyl, $C_1$-$C_4$ alkoxy, $C_6H_5$, $CH_2C_6H_5$ or halogen.

7. The ophthalmic device material of claim 6 wherein in formula [II]:
A is H or $CH_3$;
B is $(CH_2)_m$;
m is 1-5;
Y is nothing or O;
w is 0-1; and
D is H.

8. The ophthalmic device material of claim 7 wherein the ophthalmic device material comprises a monomer selected from the group consisting of: benzyl methacrylate; 2-phenylethyl methacrylate; 4-phenylbutyl methacrylate; 5-phenylpentyl methacrylate; 2-benzyloxyethyl methacrylate; and 3-benzyloxypropyl methacrylate; and their corresponding acrylates.

9. The ophthalmic device material of claim 3 wherein the ophthalmic device material comprises a cross-linking agent.

10. An intraocular lens comprising the chromophore of claim 1.

11. An ophthalmic device comprising the ophthalmic device material of claim 3.

12. The ophthalmic device of claim 11 wherein the ophthalmic device is selected from the group consisting of an intraocular lens; a contact lens; a keratoprosthesis; and a corneal inlay or ring.

* * * * *